United States Patent [19]

Thal

[11] Patent Number: 5,658,313
[45] Date of Patent: Aug. 19, 1997

[54] KNOTLESS SUTURE ANCHOR ASSEMBLY

[76] Inventor: Raymond Thal, 11321 Bright Pond La., Reston, Va. 22094

[21] Appl. No.: 678,602

[22] Filed: Jul. 15, 1996

Related U.S. Application Data

[62] Division of Ser. No. 471,508, Jun. 6, 1995, Pat. No. 5,569,306.

[51] Int. Cl.$^6$ ............................................. A61B 17/00
[52] U.S. Cl. ........................... 606/232; 606/73; 606/75; 24/357; 24/358; 24/711.4
[58] Field of Search ..................... 606/232, 75, 73, 606/148, 213, 215, 139; 24/357, 358, 360, 362, 706.2, 706.3, 707.9, 708, 711.4, 711.5

[56] References Cited

U.S. PATENT DOCUMENTS

| | | | |
|---|---|---|---|
| 1,494,233 | 5/1924 | Fudge | 24/362 |
| 4,007,743 | 2/1977 | Blake . | |
| 4,532,926 | 8/1985 | O'Holla . | |
| 4,537,185 | 8/1985 | Stednitz . | |
| 4,632,101 | 12/1986 | Freedland . | |
| 4,718,147 | 1/1988 | Fujinami | 24/706.2 |
| 4,721,103 | 1/1988 | Freedland . | |
| 4,870,957 | 10/1989 | Goble et al. | 623/13 |
| 4,898,156 | 2/1990 | Gatturna et al. . | |
| 4,946,468 | 8/1990 | Li . | |
| 5,013,316 | 5/1991 | Goble et al. . | |
| 5,037,422 | 8/1991 | Hayhurst et al. . | |
| 5,084,050 | 1/1992 | Draenert . | |
| 5,102,421 | 4/1992 | Anspach, Jr. . | |
| 5,141,520 | 8/1992 | Goble et al. . | |
| 5,192,303 | 3/1993 | Gatturna et al. . | |
| 5,207,679 | 5/1993 | Li . | |
| 5,224,946 | 7/1993 | Hayhurst et al. . | |
| 5,236,438 | 8/1993 | Wilk | 606/215 |
| 5,236,445 | 8/1993 | Hayhurst et al. . | |
| 5,258,016 | 11/1993 | DiPoto et al. . | |
| 5,318,578 | 6/1994 | Hasson | 606/139 |
| 5,356,413 | 10/1994 | Martins et al. . | |
| 5,358,511 | 10/1994 | Gatturna et al. . | |
| 5,370,661 | 12/1994 | Branch | 606/232 |
| 5,370,662 | 12/1994 | Stone et al. . | |
| 5,372,146 | 12/1994 | Branch . | |
| 5,372,599 | 12/1994 | Martins . | |
| 5,374,268 | 12/1994 | Sander | 606/72 |
| 5,383,905 | 1/1995 | Golds et al. . | |
| 5,400,805 | 3/1995 | Warren . | |
| 5,500,000 | 3/1996 | Feagin et al. | 606/232 |
| 5,545,180 | 8/1996 | Le et al. | 606/232 |
| 5,549,619 | 8/1996 | Peters et al. | 606/213 |

Primary Examiner—Jeffrey A. Schmidt
Attorney, Agent, or Firm—Hoffman, Wasson & Gitler

[57] ABSTRACT

A knotless suture anchor assembly for the attachment or reattachment or repair of tissue to a bone mass. The assembly allows for an endoscopic or open surgical procedure to take place without the requirement of tying a knot for reattachment of tissue to bone mass. A spike member is inserted through tissue mass through a loop and inserted into a dowel-like hollow anchoring sleeve which has been inserted into a bone mass. The spike member is securely fastened or attached to the anchoring sleeve with a ratcheting mechanism thereby pulling or adhering (attaching) the tissue to the bone mass.

4 Claims, 9 Drawing Sheets

KNOTLESS SUTURE ANCHOR ASSEMBLY

This is a divisional of application Ser. No. 08/471,508, filed on Jun. 6, 1995, now U.S. Pat. No. 5,569,306.

BACKGROUND OF THE INVENTION

1. Field of the Invention

The present invention relates to devices or assemblies used in tissue repair. More particularly, the assembly enables the attachment together or repair of portions of biological tissue (i.e., tendons or ligaments) onto a bone surface.

2. Description of the Background Art

Soft tissues, such as tendons and ligaments, generally are attached to bone by small collagenous fibers. These connections are strong but permit the tendons and ligaments to be flexible. When a tissue is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunnelling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as protheses, to bone. A suture anchor is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

A primary object of the present invention is to provide a suture anchor assembly which is easy to use and install.

Another object of the present invention is to provide a suture anchor assembly which allows for secure attachment of soft tissue to bone without the use or requirement of tying a knot.

Still another object of the present invention is to provide a suture anchor assembly which is compact and allows a surgeon to easily guide the tissue into a bone anchoring sleeve to enhance the security of the repair.

Still another object of the present invention is to provide an anchor assembly which allows for passage through soft tissue in a singular fashion without the need for additional instrumentation for passing the suture separately through the soft tissue to be repaired.

SUMMARY OF THE INVENTION

In accordance with the above objects, the present invention is a knotless suture anchor assembly for attachment or reattachment of biological soft tissue to bone. The unique knotless suture anchor assembly includes a hollow anchoring sleeve which is installed into a bone mass. The anchoring sleeve can have a closed pointed drill end or be totally cylindrical in shape. The hollow anchoring sleeve can be ribbed or threaded on its exterior for secure attachment to the bone or embody varying types of anchor configurations to facilitate a strong bond with the bone mass. A number of prior patents disclose configurations for the exterior of a bone anchor which are within the contemplation of the invention for use as the anchoring means for the exterior of the hollow anchoring sleeve.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying exterior structures which may embody the anchoring sleeve portion of the invention. These patents disclose various means and mechanisms for anchoring a device to a bone mass thus preventing pull-out of the sleeve after insertion into bone.

Further, the hollow anchoring sleeve can contain a collar on the rear portion or rear side of the hollow anchoring sleeve to control the depth of sleeve insertion into the bone and prevent excessive insertion depth.

A second component of the knotless suture anchor assembly is the spike or plug member which has on its first end a configuration which allows for easy puncturing of a soft tissue and on its second or other end a means for attachment of a suture material. The first end can be pointed or frusto-conical in shape. The spike or plug can be ribbed, beaded, threaded or expandable on its exterior surface for secure mating with the interior wall section of the hollow anchoring sleeve. The suture material which is attached to the rear end of the spike or plug member has at least one loop portion positioned at its other end. The loop portion can be the same suture material as the suture which is attached to the end of the spike or plug. Alternatively, the loop portion can be produced of a different material, other than suture, with different characteristics (i.e.—molded or metal) and can be attached to the spike or plug by a length of suture. In the alternative, the suture can be attached in one full loop on the rear end of the spike or plug member.

The spike or plug member, suture and loop portion can be all produced of the same material (i.e., molded). This would obviate need for the second end of the spike or plug member to have means for attachment of the suture thereto.

The spike or plug member is inserted during an open or endoscopic procedure, or the like, through the soft tissue and its piercing or pointed end is then threaded through the loop portion formed in the suture material prior to its ultimate insertion into the anchoring sleeve to facilitate a secure mating. Once the spike or plug member is threaded through the tissue and then through the loop portion and is inserted into the hollow anchoring sleeve, it is then securely attached through pressure by the surgeon into the sleeve. This attachment of the spike member to the hollow anchoring sleeve can be accomplished in one step or in a number of depth control steps (i.e., ratchets) to fine tune the tightness of the repair. This ratchet effect can be accomplished by a series of beads, ribs, thickening or the like on the exterior of the spike component. These would mate with the interior of the anchor sleeve. This allows for the tissue to be tightly attached to the bone mass. The unique device obviates the need for the surgeon to tie a knot with the suture material for reattachment of tissue to bone. Endoscopic procedures and some open surgical procedures are extremely difficult and must be completed in a very tight space. Obviation of the need of tying a knot is extremely beneficial and innovative.

Further, the unique knotless anchoring sleeve may be formed in one complete assembly. The hollow anchoring sleeve has one end for insertion into the bone mass and a suture material attached at its other end. The other end of the suture is attached to the rear end of the spike or plug member. This spike or plug member can then be inserted directly through the tissue mass and into the hollow anchoring sleeve for attachment of soft tissue to bone. The length of the suture material is adjustable based upon the requirements of the surgical procedure. The procedure is a process wherein first the spike or plug member which may be ribbed, beaded, threaded or expandable is inserted through the soft tissue and then directly into the hollow anchoring sleeve. The hollow anchoring sleeve is then inserted into the bone mass. The soft tissue is thus secured to the bone mass. Tension is then adjusted by the depth of the anchor insertion and/or the ribbed, beaded, threaded or expandable mechanism for mating the spike member into the hollow anchoring sleeve.

In addition, it is within the contemplation of this invention to produce a knotless suture anchor assembly that includes a spike or plug member which can act as the bone anchor and spike without the necessity of a hollow anchoring sleeve. The spike or plug member, suture and loop portion is identical to that described above with the added feature of the spike or plug member having a bone anchoring means on its exterior surface.

As previously described, the suture and loop portion can vary in shape and be produced of the same or different materials.

Numerous other features of various embodiments of the knotless suture anchor assembly will be apparent from the following detailed description and the accompanying drawings.

DETAILED DESCRIPTION OF THE PRESENT INVENTION

Figures 1A, 1B, 1C, 1D:
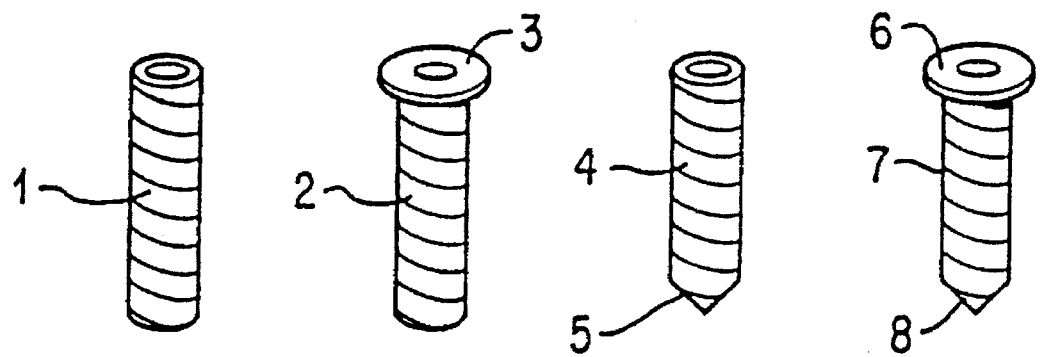
FIGS. 1a, 1b, 1c and 1d are perspective views of a hollow anchoring sleeve made in accordance with the present invention.

Referring now to FIG. 1, the knotless suture anchor assembly of the present invention contains as one integral component a hollow anchoring sleeve for installation and attachment to a bone mass. The hollow anchoring sleeve 1, as shown in FIG. 1a, is cylindrical in shape and possesses ribs or threads on its exterior. The device can also contain or be configured with prongs, umbrella spokes, have threads, be expandable, or have wedges, on its exterior, for secure attachment with the bone mass. These exterior attachment features are known to the industry and incorporated herein by reference.

FIG. 1b illustrates an alternate embodiment of the hollow anchoring sleeve 2 having a collar 3 to control depth of bone penetration. The collar prevents the sleeve from being forced too deep into the bone mass when the spike or plug member is inserted.

FIG. 1c illustrates an alternate embodiment of the hollow anchoring sleeve 4 wherein the sleeve has a pointed closed end 5 for ease of penetration into a bone mass.

FIG. 1d illustrates a hollow anchoring sleeve 7 with a collar 6 and a closed pointed end 8 as an alternate construction.

As pointed out in the Summary of the Invention, the hollow anchoring sleeve may also be shaped or configured with any means to secure said structure to a bone mass. The hollow anchoring sleeve may include a threaded exterior as disclosed in U.S. Pat. No. 5,370,662, incorporated herein by reference. Further, the device may be expandable as disclosed in U.S. Pat. No. 5,084,050, incorporated herein by reference. A configuration such as disclosed in U.S. Pat. Nos. 5,037,422; 5,224,946; and 5,236,445 are also contemplated by the invention and these disclosures are incorporated by reference. Harpoon configurations such as disclosed in U.S. Pat. Nos. 5,141,520 and 5,102,421 are also contemplated for the hollow anchoring sleeve and incorporated herein by reference.

It is also within the contemplation of the present invention to configure the anchoring sleeve in a harpoon-type fashion such as disclosed by U.S. Pat. Nos. 4,632,101 and 4,721,103 for secure anchoring within the bone mass. U.S. Pat. Nos. 4,898,156; 5,207,679; 4,946,468; and 5,192,303 disclose anchoring mechanisms which can be utilized for the hollow sleeve member for installation within a bone mass. These patents are incorporated by reference and fall within the contemplation of the present invention for methods or means for anchoring the sleeve to the bone mass. It is also within the contemplation of the present invention to configure this dowel-like hollow sleeve in any fashion to securely attach same to a bone mass.

The interior surface of the hollow anchoring sleeve is ribbed, beaded, threaded, expandable or smooth for secure engagement with said exterior surface of said spike member.

Figure 2:
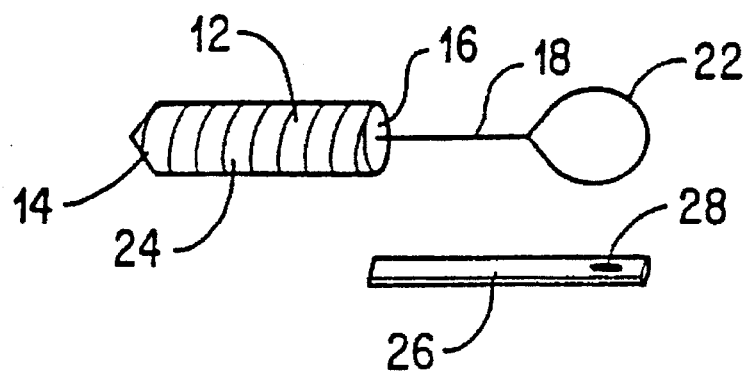
FIG. 2 is a perspective view of a spike member with suture element of the present invention.

FIG. 2 shows a perspective view of the spike plug member with suture element embodying the present invention. Spike or plug member 12 is preferably cylindrical in shape with a sharp first end 14 and a second end 16 wherein the suture element 18 is attached. The suture element 18 has at its distal end a loop or ring 22. The loop or ring portion 22 can be constructed of the same suture material as suture element 18 or it can be a separate molded material attached to the suture element 18 and loop portion 22 may be one molded component and attached to spike member 12 at end 16 or they may be all (spike, suture element and loop portion) one entire molded component. Further, the suture element 18, alone, can be made from any type suture material which has been approved for surgical procedures for attachment of tissue to bone. The spike or plug member can form any shape so long as it mates with the hollow cylindrical sleeve as described above. The exterior of the spike or plug member 12 may be ribbed or threaded 24 as depicted in FIG. 2 or may be beaded or expandable to allow for a secure tight fit with the inner hollow cylinder of the anchoring sleeve. Once inserted into a hollow anchoring sleeve, the exterior surface of the spike or plug member 12 engages the inner surface of the sleeve and can be ratcheted down to produce the desired tight fit. This ratcheting effect allows for fine tuning and tightening of the soft tissue to the bone during repair. The length of the suture connection 18 is variable and may be adjusted prior to selection of a tool or during surgical procedure through any appropriate means. Likewise, the diameter of the loop 22 is adjustable and may be replaced by one long strip of suture-like material, or molded strip, 26 having a slot or hole 28 for insertion of the spike or plug member once it has been passed through a tissue for attachment.

Figure 3:
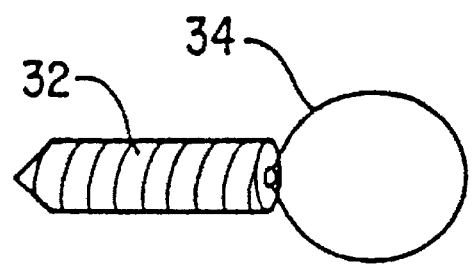
FIG. 3 is a perspective view of an alternate embodiment of a spike member with suture element of the present invention.

FIG. 3 illustrates an alternate embodiment of the spike member with suturing material. The spike member 32 has attached at its rear end one complete loop of suture 34 which also has an adjustable diameter for various thicknesses of tissue reattachment.

Figure 4:
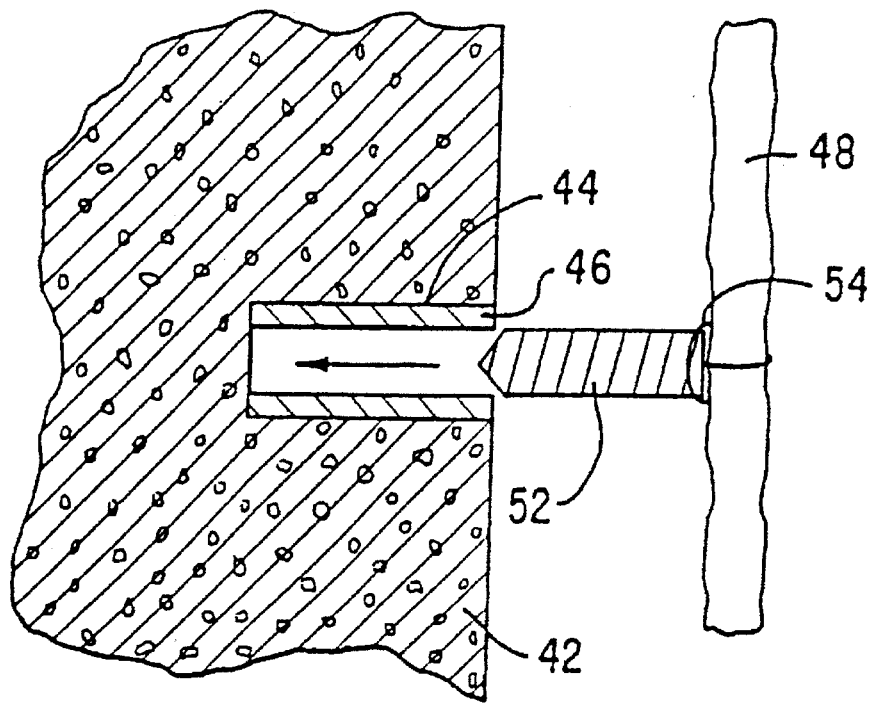
FIG. 4 illustrates usage of the preferred embodiment of the present invention in conjunction with a bone mass and tissue during surgical reattachment.

Referring now to FIG. 4, there is illustrated a process for reattachment of tissue to bone mass. Bone mass 42 has a slot or hole 44 wherein a hollow anchoring sleeve 46 has been inserted. A tissue 48 has inserted therein a spike member 52 threaded through loop 54 for reattachment to the bone mass 42.

Figure 5:
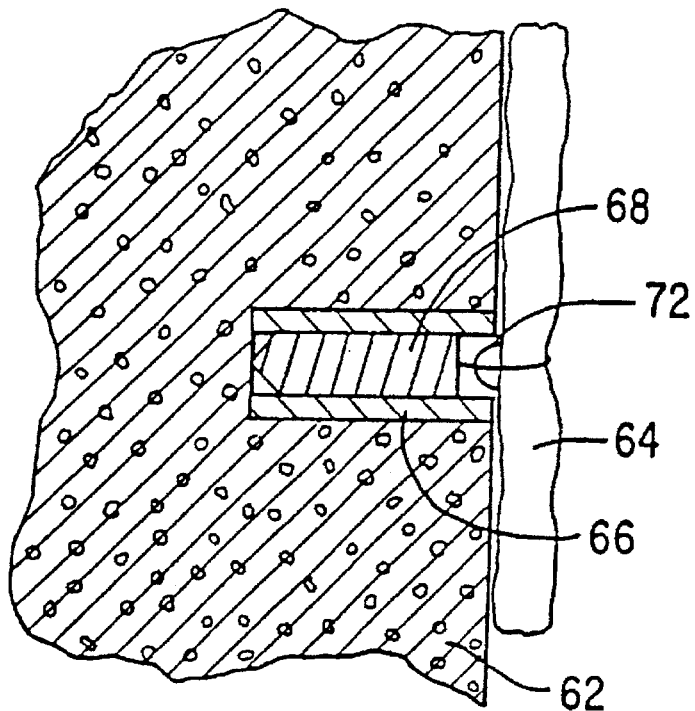
FIG. 5 illustrates the preferred embodiment of the invention in place after attachment of tissue to bone mass has been completed.

FIG. 5 depicts the knotless suture anchor assembly in place after the surgical procedure has been completed. Bone mass 62 has tissue 64 attached or reattached thereto.

The surgical procedure for reattaching or attaching tissue to bone mass includes first installation of the hollow anchoring sleeve 66. Secondly, the spike member 68 is inserted through the tissue 64 and then through at least one loop portion 72. The spike 68 with tissue 64 securely attached thereto is then secured directly into the anchoring sleeve 66 for attachment of tissue 64 to bone mass 62 completing the method.

Figure 6:
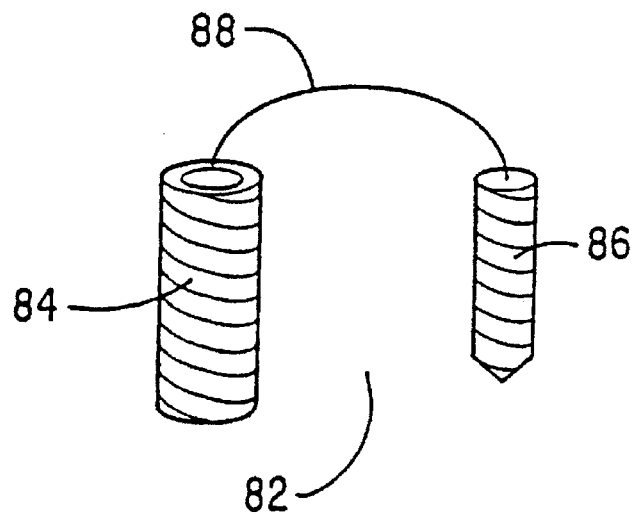
FIG. 6 illustrates an alternate embodiment of the present knotless suture anchor assembly.

Referring now to FIG. 6, there is disclosed an alternate embodiment of the knotless suture anchor system 82. There is disclosed a hollow anchoring sleeve 84 having attached thereto a spike or plug member 86 by a suture element 88. As discussed and described above in a preferred embodiment of the invention, the hollow anchoring sleeve 84 may take the shape or form of almost any type of anchor device. All the patents listed above are incorporated by reference. Configurations of the hollow anchoring sleeve having a collar, as well as a configuration incorporating any type of umbrella expansion means or threading on the exterior or interior of the sleeve are contemplated as being part of the present invention. Further, the spike or plug member 86 is preferably threaded on its exterior with a pointed end for insertion through a tissue element. This may take the form of any structure and preferably has an exterior which is ribbed, beaded, threaded, smooth or expandable. Likewise, the suture element 88 may be made of any acceptable surgical suture material and in addition is lengthened based upon thickness and need requirements.

Figure 7:
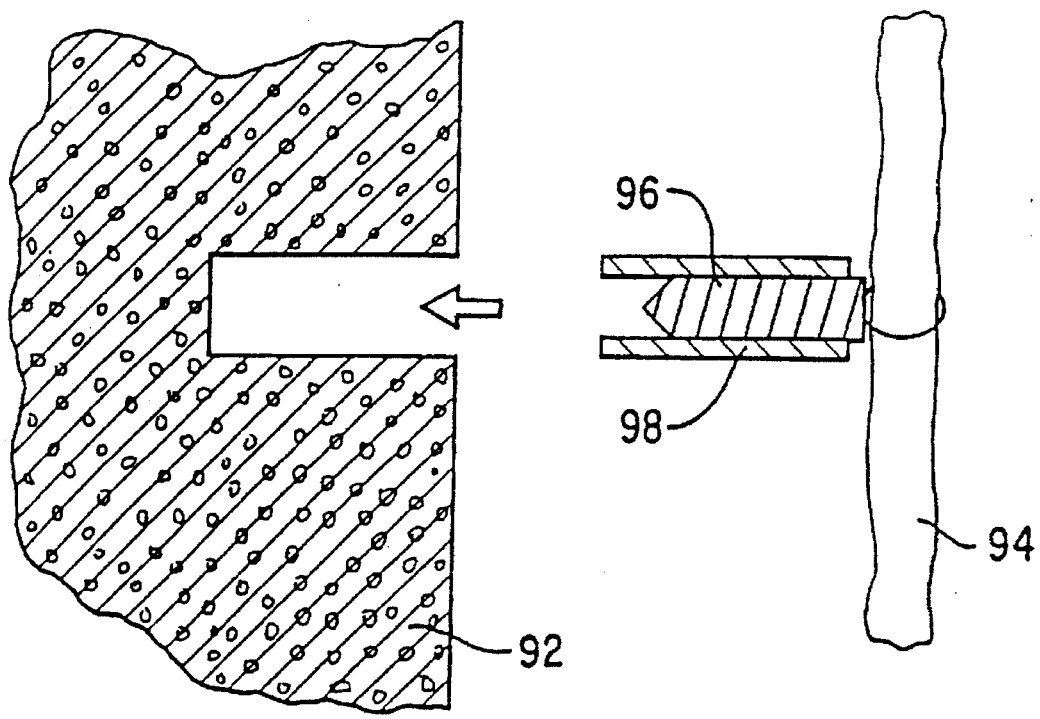
FIG. 7 illustrates the procedure for attachment of tissue to bone mass for the embodiment as outlined in FIG. 6.

Referring now to FIG. 7, there is depicted the initial step in the process for attachment of tissue to bone utilizing the alternate embodiment of FIG. 6. A spike member 96 is inserted through a tissue 94 and into a hollow anchoring sleeve 98. The assembly is then attached to a bone mass 92.

Figure 8:
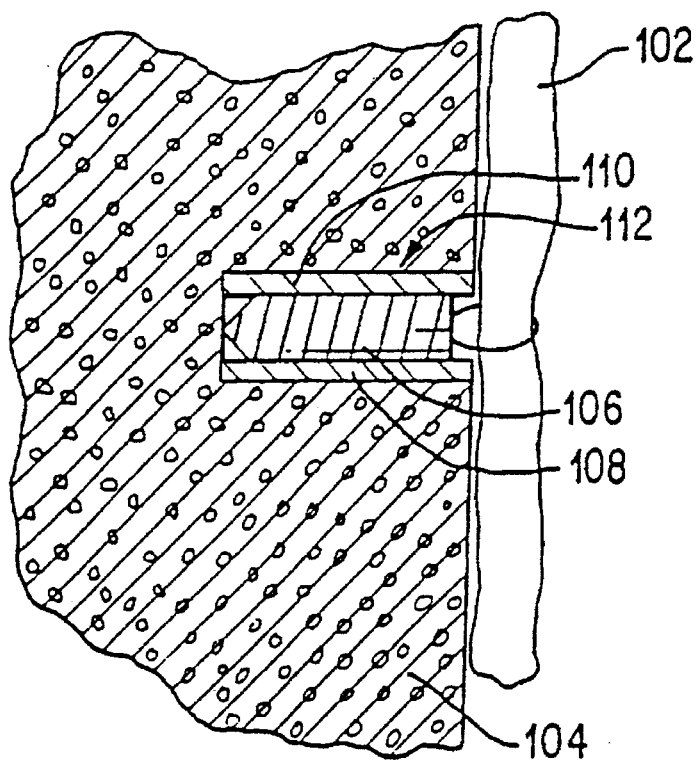
FIG. 8 illustrates the embodiment of FIG. 6 showing tissue attached to bone.

Referring now to FIG. 8, there is disclosed the completed attachment or reattachment of tissue 102 to bone mass 104.

The spike or plug member 106 is inserted through said tissue 102 and then inserted into hollow anchoring sleeve 108 for complete attachment to bone mass 104 at a previously drilled section 110. This enables one to surgically reattach the tissue 102 to bone mass 104 in a virtual one step process.

Additionally, the process embodied by FIG. 8 may be undertaken in two steps. First, the spike member 106 is inserted through the soft tissue 102 and into the hollow anchoring sleeve 108.

Secondly, the entire assembly 112, spike member 106 which has been inserted into the sleeve 108, is inserted into the bone mass 104. Regardless of the process used, the repair tightness is adjusted by the depth of anchor insertion into bone and/or the ratcheting effect of the spike in the anchor sleeve.

Figure 9:
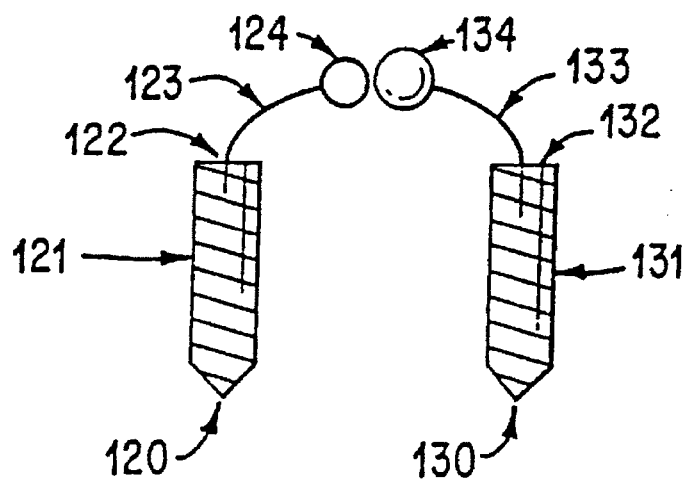
FIG. 9 illustrates the spike components for an alternate embodiment of a knotless suture anchor assembly in accordance with the present invention.

FIG. 9 depicts an alternate preferred embodiment. First and second spike or plug assembly members, 120 and 130, respectively, are depicted for the knotless suture anchor assembly. There is disclosed first spike or plug assembly member 120 having spike means 121 for insertion into a hollow anchoring sleeve as depicted in FIGS. 1a–1d. Spike or plug member 121 is preferably threaded with a pointed end for insertion through a tissue element and secure fixation with said hollow anchoring sleeve. The spike or plug member may take the form of any Structure and preferably has an exterior which is ribbed, threaded, beaded, expandable or smooth. The diameter of thickness of the member is preferably equal to or incrementally less than the entire diameter of the hollow anchoring sleeve for a secure fit. In situations where ribs, threads, beads, or the like, are utilized on the spike member, the diameter of the member with protrusions may initially exceed the inner diameters of the hollow anchoring sleeve and would deform upon insertion.

The rear end 122 of the spike member 121 has attached or tied thereto a suture element 123. The suture element 123 has attached or molded therewith a catch device, such as a ring element, 124 which is preferably rigid. The spike member 121, suture element 123 and catch device (ring element) 124 may be made of separate materials or molded together as one piece. In addition, the spike member 121 and suture element 123 may be molded as one element or the suture element 123 and catch device (ring element) 124 may be molded as one element.

Second spike assembly member 130 includes a spike or plug member 131 for insertion into a hollow anchoring sleeve as depicted in FIGS. 1a–1d. The element 131 is described above and can be the same or different as spike element 121. To the rear end 132 of the spike member 131 there is tied or attached a suture element 133. The suture element 133 has attached or molded therewith a spherical, or the like, stop means 134.

As stated above, the three components, spike member 131, suture element 133 and stop means 134 can be combined as separate components or molded together as one entire component or a combination of two components.

Figure 10:
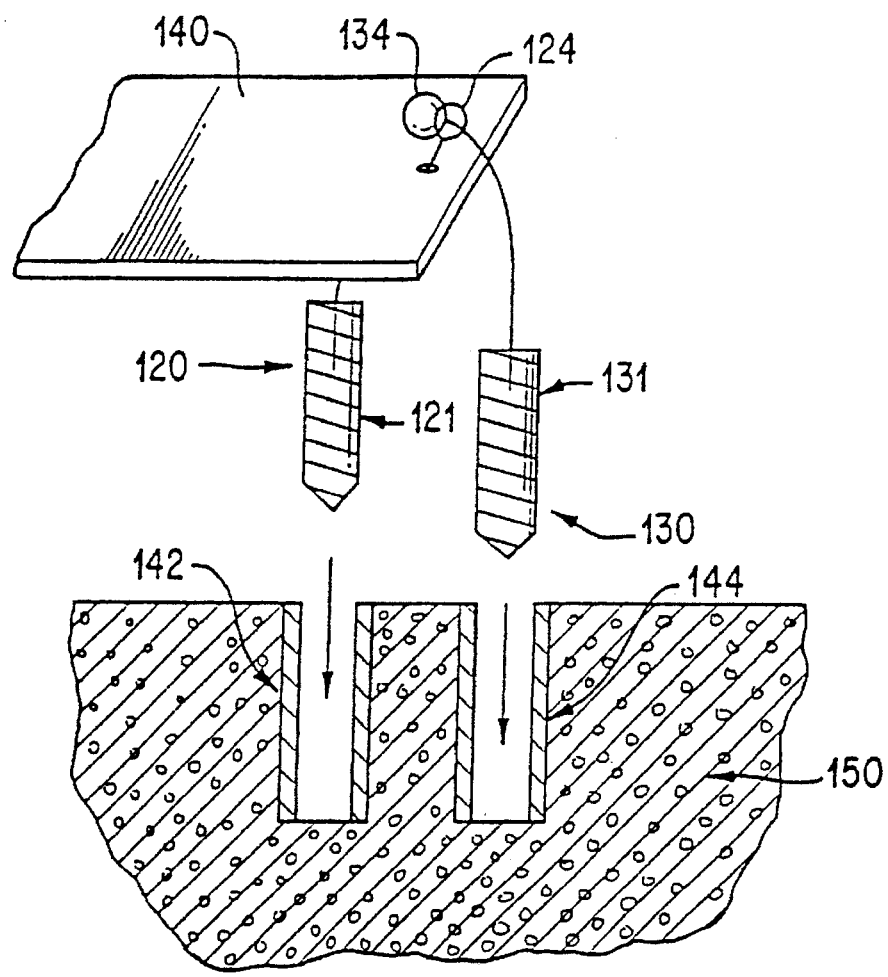
FIG. 10 is a partial exploded view of the spike components and hollow anchoring sleeves inserted through soft tissue and mated together for attachment of tissue to bone mass.
Figure 11:
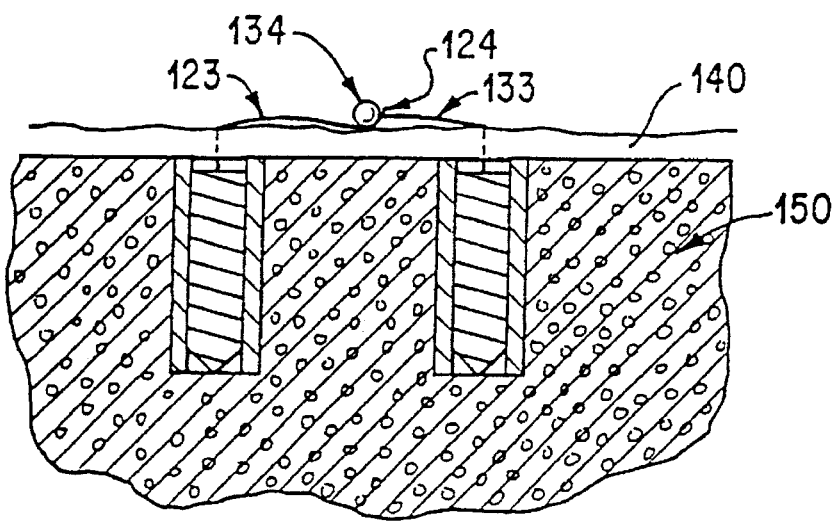
FIG. 11 is an illustration of the embodiment of FIGS. 9 and 10 wherein tissue is attached to a bone mass in a secure manner.

Referring now to FIG. 10, first spike assembly member 120 is inserted into tissue 140. The spike member 121 can be inserted into a hollow anchoring sleeve 142 either before or after the hollow anchoring sleeve 142 is inserted into bone mass 150. Spike member 131, of spike member assembly means 130, is inserted through catch device (ring element) 124, of spike member assembly 120. The spike member 131 is then inserted through tissue 140 and then into hollow anchoring sleeve 144, or directly into hollow anchoring sleeve 144. The hollow anchoring sleeve 144 can be anchored to bone mass 150 before or after spike member 131 has been inserted therein. The stop means 134 mates with catch device (ring element) 124 dragging the tissue into a secure fit with bone mass 150 (See FIG. 11.)

Once the spike members have been inserted into the hollow anchoring sleeves they can be ratcheted down to a desired depth to adjust the tightness of the soft tissue repair to bone mass. Tightness can also be adjusted by the depth of anchor sleeve insertion into the bone mass.

Stop means 134 may be spherical with a diameter greater than catch device (ring element) 124, or may be any shape which would facilitate a mating with the catch device. Likewise, the catch device need not be circular, but requires only an opening to allow passage of a spike member and prevent passage of the stop means. The catch device 124, depicted in FIGS. 10 and 11, can take the form of a ring, square, slot, or any shape that will cooperate and hold stop means 134 from being pulled therethrough.

Figure 12:
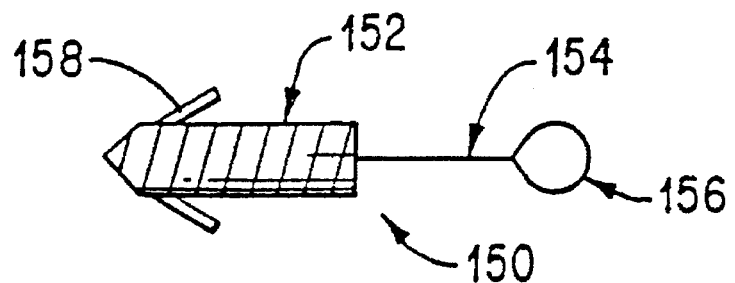
FIG. 12 illustrates an alternate embodiment of the present invention.
Figure 13:
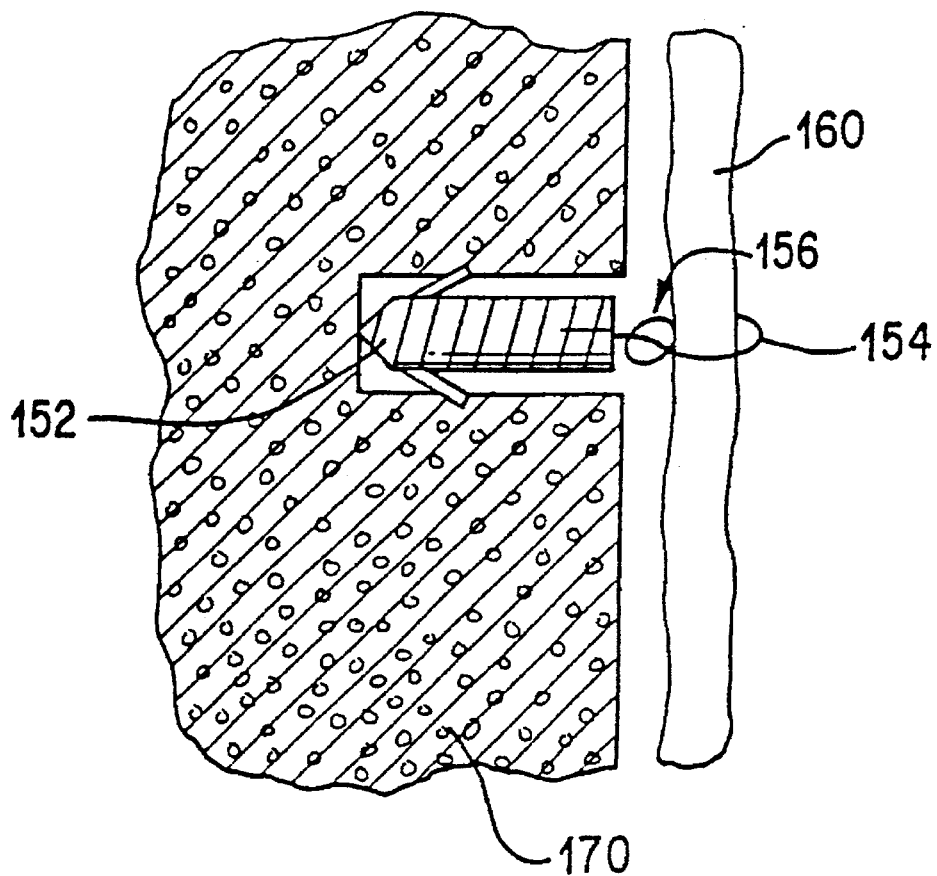
FIG. 13 illustrates the embodiment of FIG. 12 in conjunction with a bone mass and tissue during surgical reattachment.

Knotless suture anchor assembly 150 is an alternate embodiment of the present invention (FIG. 12). The assembly 150 includes a spike/anchor means 152, a suture element 154, and a loop portion 156. As discussed above, the suture element 154 and loop portion 156 may be made of the same or different materials. In addition, the spike/anchor means 152 can be molded with the suture element 154 and loop portion 156 as one piece or as separate components, as desired. The spike/anchor means can be configured, as desired, to securely attach the assembly 150 to a bone mass. The spike/anchor means may include all the attachment means as described above for the hollow anchoring sleeve such as harpoon type means 158, prongs, umbrella spokes, threads, wedges or the like.

Additionally, the entire suture element 154 may be configured in a complete loop as depicted in FIG. 3, or may merely have a slit along its length as depicted in FIG. 2.

When performing a procedure, loop portion 156 is pulled through soft tissue 160. Once the loop portion 156 has been pulled through the soft tissue 160, the spike/anchor means 152 is inserted through the loop portion 156 and directly into bone mass 170 for attachment of tissue 160 to bone mass 170. The length of suture 154 and depth of insertion of the spike/anchor means 152 controls the secure tightness of repair of tissue 160 to bone mass 170, and is adjusted as desired.

Figure 14:
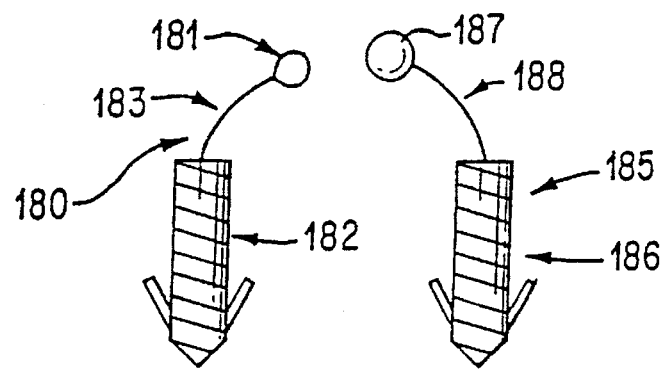
FIG. 14 illustrates an alternate embodiment of the present invention.

FIG. 14 depicts an embodiment of the present invention wherein a first knotless suture anchor assembly 180 is provided as described in accordance with knotless suture anchor assembly 150, as depicted in FIG. 12 and previously described. A second knotless suture anchor assembly 185 is also provided to being used in conjunction with assembly 180 to perform a surgical attachment of tissue to bone.

Figure 15:
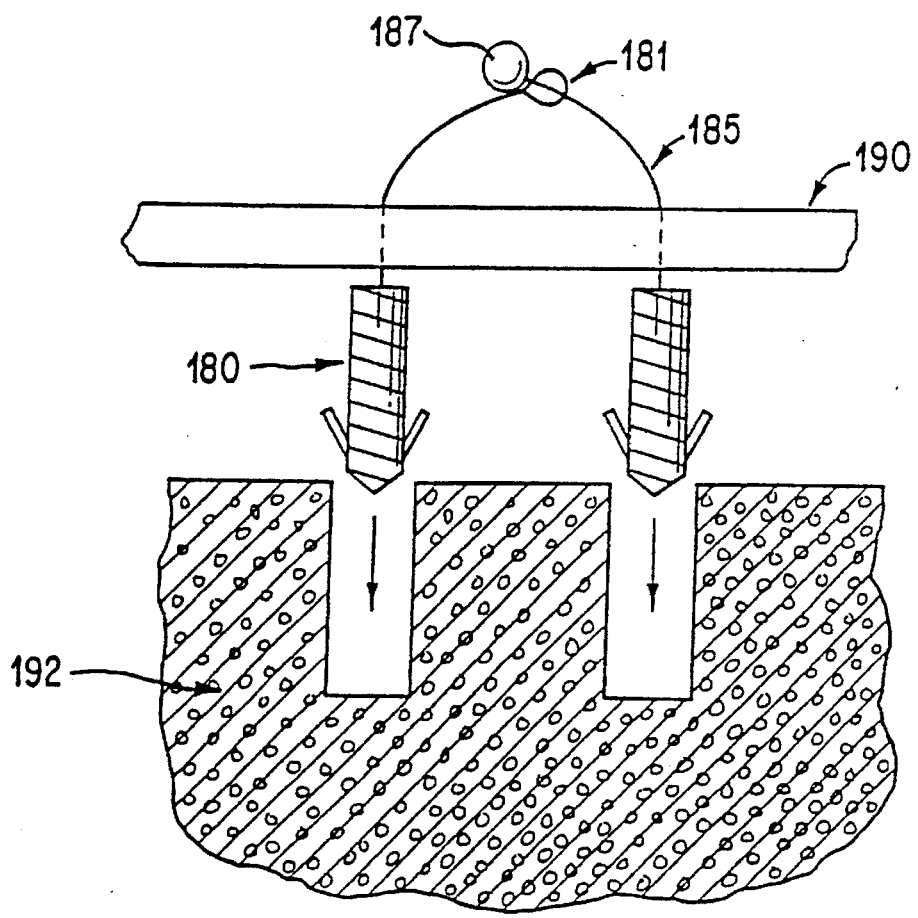
FIG. 15 illustrates the embodiment of FIG. 14 in conjunction with a bone mass and tissue during surgical reattachment.
Figure 16:
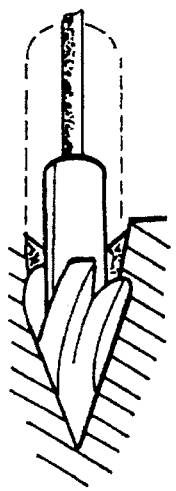
FIG. 16 is an enlarged perspective view of a harpoon anchor.
Figure 17:
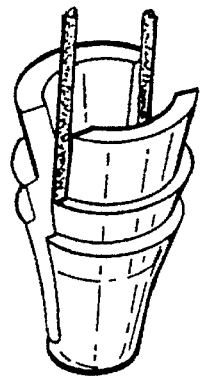
FIG. 17 is an enlarged perspective view of an umbrella-like anchor.
Figure 18:
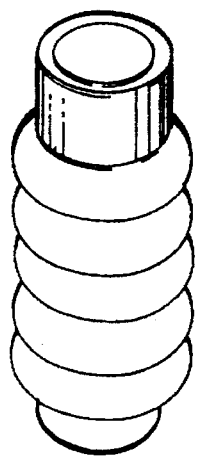
FIG. 18 is an enlarged perspective view of a ribbed anchor.
Figure 19:
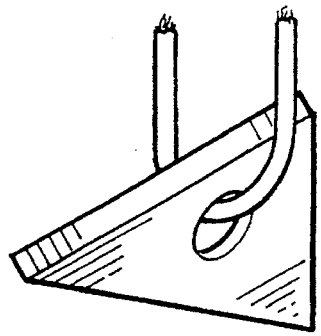
FIG. 19 is an enlarged perspective view of a wedge-like anchor.
Figure 20:
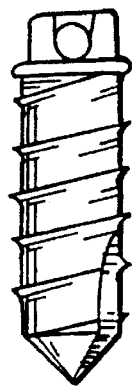
FIG. 20 is an enlarged perspective view of a threaded anchor.
Figure 21:
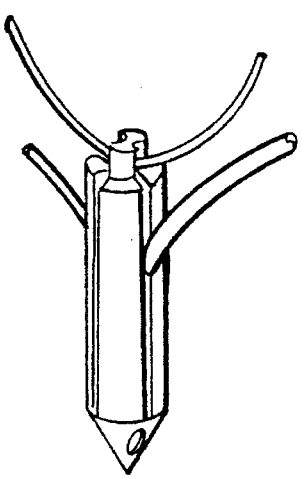
FIG. 21 is an enlarged perspective view of a pronged anchor.
Figure 22:
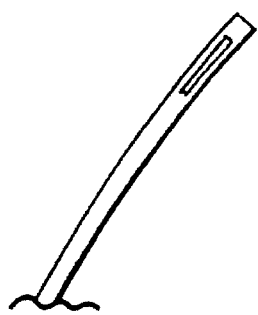
FIG. 22 is an enlarged perspective view of a slotted catch means.
Figure 23:
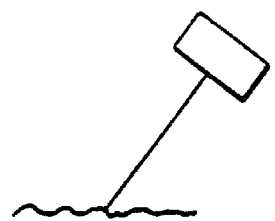
FIG. 23 is an enlarged perspective view of a square shaped catch means.
Figure 24:
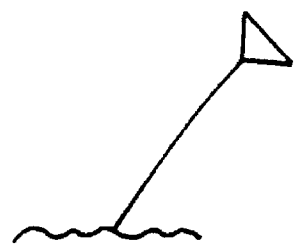
FIG. 24 is an enlarged perspective view of a triangular shaped catch means.

First the catch device 181 is inserted through soft tissue 190 from the underside of the tissue first (see FIG. 15). Then a spike/anchor means 182 of assembly 180 is inserted into the bone mass 192. Next, a spike/anchor means 186 (with bone anchoring features) is threaded through catch device 181 and inserted into bone mass 192. Stop means 187 mates with catch device 181 and the sutures 183 and 188 are pulled taught to securely attach soft tissue 190 to bone mass 192.

In many situations throughout the discussion above, the terminology secure attachment of soft tissue to bone has been used. Such terminology refers to the attachment or reattachment of tissue to bone through the insertion of a spike member into a hollow anchoring sleeve or a spike/anchor means into a bone mass. In the former situation, the spike member can seat into the sleeve in a one step mating procedure or be inserted and ratcheted down in a step wise fashion into the sleeve. Either situation will function effectively and selection is based upon the instant facts of the surgical procedure. Further, the sleeve itself may be seated in the bone mass at varying depths. Again, such depth is a selection based upon the facts of the instant procedure. In the latter situation, where a spike/anchor means is used, depth of insertion of the device into the bone is a selection or choice of the surgeon during the procedure. In all situations, the spike member or spike/anchor means is designed not to back up or exit once mated with the sleeve, ratcheted down into the sleeve, or inserted into the bone mass to avoid and prevent withdrawal therefrom.

While a preferred embodiment of the invention in a knotless suture anchor system has been shown and described herein, it should be understood that the present disclosure is made by way of example only and that variations to the structure shown and its use are possible within the scope of this disclosure without departing from the subject matter coming within the scope of the following claims, and a reasonable equivalency thereof, which claims we regard as our invention.

What is claimed is:

1. A knotless suture anchor assembly for attachment of tissue to a bone mass, comprising:

a first knotless suture anchor assembly comprising a first anchor means for attachment to said bone mass, said first anchor means having a first end and a second end, said first end having a suture element attached thereto, wherein said suture element has a catch means located along its length for passing through said soft tissue, and a second knotless suture anchor assembly comprising a second anchor means for attachment to said bone mass, said second anchor means having a first end and a second end, said first end of said second anchor means having a suture element attached thereon, wherein said suture element has a stop element located along its end for engagement with said catch device of said first knotless suture anchor assembly, wherein said second end of said second anchor means is for passing through said catch means of said first knotless suture anchor assembly and for insertion into said bone mass for secure attachment of said tissue to said bone mass.

2. A knotless suture anchor assembly as claimed in claim 1, wherein said first and second anchor means for attachment to said bone mass are harpoon anchors, wedge-like anchors, umbrella-like anchors, ribbed anchors, threaded anchors, or pronged anchors.

3. A knotless suture anchor assembly as claimed in claim 1, wherein said catch means of said first knotless suture anchor assembly has a circular shape, a slotted shape, a square shape, or a triangular shape, with an opening smaller than a size of said stop element of said second knotless suture anchor assembly.

4. A method for attachment of tissue to a bone mass utilizing the assembly as claimed in claim 1, comprising the steps of:

a) inserting said at least one catch means of said first knotless suture anchor assembly through said tissue;

b) installing said first anchor means for attachment to said bone mass into said bone mass;

c) inserting said second anchor means for attachment to said bone mass through said catch means; and d) installing said second anchor means into said bone mass;

wherein said stop means mates with said catch means thereby securely attaching said tissue to said bone mass.

* * * * *